US009523635B2

(12) United States Patent
Tilden (10) Patent No.: US 9,523,635 B2
(45) Date of Patent: Dec. 20, 2016

(54) APPARATUS AND METHODS OF SPECTRAL SEARCHING USING WAVELET TRANSFORM COEFFICIENTS

(71) Applicant: Scott B. Tilden, Tucson, AZ (US)

(72) Inventor: Scott B. Tilden, Tucson, AZ (US)

(73) Assignee: Rigaku Raman Technologies, Inc., Tucson, AZ (US)

( * ) Notice: Subject to any disclaimer, the term of this patent is extended or adjusted under 35 U.S.C. 154(b) by 821 days.

(21) Appl. No.: 13/922,459

(22) Filed: Jun. 20, 2013

(65) Prior Publication Data

US 2014/0379278 A1 Dec. 25, 2014

(51) Int. Cl.
  *G01N 31/00* (2006.01)
  *G01N 21/25* (2006.01)
  *G01N 23/00* (2006.01)
  *G01J 3/28* (2006.01)
  *G06F 17/14* (2006.01)

(52) U.S. Cl.
  CPC .............. *G01N 21/255* (2013.01); *G01J 3/28* (2013.01); *G01N 23/00* (2013.01); *G06F 17/148* (2013.01)

(58) Field of Classification Search
  CPC  G01N 2223/304; G01N 23/087; G01N 23/00; G01N 21/255; G06F 17/148; G01J 3/28
  USPC .............................................. 702/22, 27, 28
  See application file for complete search history.

(56) References Cited

U.S. PATENT DOCUMENTS

| | | |
|---|---|---|
| 7,283,684 B1 | 10/2007 | Keenan |
| 7,496,619 B2 * | 2/2009 | Aldroubi ................. G06T 5/001 708/446 |
| 8,412,468 B1 | 4/2013 | Kessler |
| 2002/0025490 A1 | 2/2002 | Schegolikhin et al. |
| 2005/0065440 A1 | 3/2005 | Levenson |

(Continued)

FOREIGN PATENT DOCUMENTS

WO    2004038602 A1    5/2004

OTHER PUBLICATIONS

International Search Report, PCT/US2014/043099.

*Primary Examiner* — An Do
(74) *Attorney, Agent, or Firm* — Chapin Intellectual Property Law, LLC (57) ABSTRACT

Apparatus and methods of spectral searching that employ wavelet coefficients as the basis for the searching. The disclosed apparatus and methods employ a wavelet lifting scheme to transform spectroscopic data corresponding to an unknown pure material/mixture to a vector of wavelet coefficients, compare the wavelet coefficient vector for the unknown pure material/mixture with a library of wavelet coefficient vectors for known pure materials/mixtures, and identify the closest match to the unknown pure material/mixture based on the comparison of wavelet coefficient vectors. Because the wavelet lifting scheme can generate the wavelet coefficient vectors for the unknown pure material/mixture as well as the known pure materials/mixtures to conform to a desired compression level, the disclosed apparatus and methods can perform spectral searching with increased speed and reduced memory requirements, thereby making the disclosed apparatus and methods amenable for use in hand-held instruments for on-site material identification.

17 Claims, 7 Drawing Sheets

(56) References Cited

U.S. PATENT DOCUMENTS

| | | |
|---|---|---|
| 2005/0190978 A1* | 9/2005 | Li .................... H04N 19/139 |
| | | 382/240 |
| 2005/0228295 A1 | 10/2005 | Tan |
| 2007/0198194 A1 | 8/2007 | Chait et al. |
| 2008/0024778 A1 | 1/2008 | Honda et al. |
| 2008/0080773 A1 | 4/2008 | Brady et al. |
| 2008/0300826 A1 | 12/2008 | Schweitzer et al. |
| 2009/0163369 A1 | 6/2009 | Treado et al. |
| 2010/0179934 A1 | 7/2010 | Howley |
| 2011/0237446 A1 | 9/2011 | Treado et al. |

* cited by examiner

APPARATUS AND METHODS OF SPECTRAL SEARCHING USING WAVELET TRANSFORM COEFFICIENTS

TECHNICAL FIELD

The present application relates generally to spectral searching, and more specifically to apparatus and methods of spectral searching that employ wavelet transform coefficients as the basis for the searching.

BACKGROUND

Apparatus and methods of material identification are known that employ embedded algorithms for identifying unknown pure materials or mixtures (such pure materials or mixtures also referred to herein as "pure materials/mixtures") based on the similarity between the spectra of such unknown pure materials/mixtures and the spectra of various known pure materials/mixtures stored in a database. For example, such apparatus and methods can be used to identify unknown pure materials/mixtures in diverse situations involving train derailments, overturned vehicles on roads or highways, industrial and chemical leaks or explosions, the illegal drug trade, etc. Further, such apparatus can include Raman spectrometers, infrared or near infrared spectrometers, fluorescence spectrometers, mass spectrometers, nuclear magnetic resonance (NMR) spectrometers, etc., which can employ algorithms configured to implement spectral database searching based on traditional cross correlation techniques, Euclidean techniques, derivative techniques, etc.

For example, conventional apparatus and methods of material identification that employ algorithms based on cross correlation techniques typically cross correlate the spectrum of an unknown pure material or mixture (such a pure material or mixture also referred to herein as a "pure material/mixture") with the spectral data set for each known pure material/mixture stored in a database. Because the cross correlation of spectra having varying spectral intensity ranges often leads to erroneous results, such conventional apparatus and methods typically operate on spectral intensity values that have been normalized between 0 and 1. Such conventional apparatus and methods can then identify the closest match to the unknown pure material/mixture based on the spectral data set that provides the highest positive correlation coefficient (also referred to herein as the "hit quality index").

Further, conventional apparatus and methods of material identification that employ algorithms based on Euclidean techniques typically subtract the spectral intensity value at each wavelength of the spectrum of an unknown pure material/mixture point-by-point from the spectral intensity value at each wavelength of the spectra of known pure materials/mixtures stored in a database. Such conventional apparatus and methods can sum the subtracted spectral intensity values to generate a hit quality index for each known pure material/mixture in the database. The conventional apparatus and methods can then identify the closest match to the unknown pure material/mixture based on the spectral data set that provides the lowest overall subtracted-sum value, which corresponds to the highest hit quality index.

Moreover, conventional apparatus and methods of material identification that employ algorithms based on derivative techniques typically subtract the derivative of the spectrum of an unknown pure material/mixture point-by-point from the derivative of the spectrum of each known pure material/mixture stored in a database. For example, such a derivative can be expressed as the difference between the spectral intensity value at a given wavelength "w" and the spectral intensity value at the wavelength "w−1". Such conventional apparatus and methods can sum the subtracted derivative values to generate a hit quality index for each known pure material/mixture in the database. The conventional apparatus and methods can then identify the closest match to the unknown pure material/mixture based on the spectral data set that provides the lowest overall derivative subtracted-sum value, which corresponds to the highest hit quality index. It is noted that such derivative techniques can be used in combination with cross correlation techniques. Moreover, like the conventional apparatus and methods that employ algorithms based on the cross correlation technique, the conventional apparatus and methods that employ algorithms based on the Euclidean and derivative techniques typically operate on spectral intensity values that have been normalized between 0 and 1.

However, conventional apparatus and methods of material identification that employ algorithms based on traditional techniques, such as the cross correlation, Euclidean, and derivative techniques, can have drawbacks. For example, the spectrum of an unknown pure material/mixture can sometimes have a sloping baseline due to, e.g., problems with filtering, natural fluorescence in the unknown pure material/mixture, a trace contaminant that creates fluorescence in the unknown pure material/mixture, ambient light, laser bleed through, etc. Such a sloping baseline in the spectrum of an unknown pure material/mixture can, in turn, cause varying degrees of mathematical error and uncertainty in the results generated using the cross correlation, Euclidean, and derivative techniques discussed above.

Further, the spectrum of an unknown pure material/mixture can sometimes have poor signal-to-noise characteristics, causing spectral peaks to be barely recognizable amid the noise across the spectrum. Such poor signal-to-noise characteristics of the spectrum of an unknown pure material/mixture can also cause varying degrees of mathematical error and uncertainty in the results generated using the cross correlation, Euclidean, and derivative techniques discussed above, and can be effectively amplified by those techniques that involve a difference calculation.

In addition, to achieve increased success in material identification, it is typically necessary for conventional apparatus and methods to determine the similarity between the spectrum of an unknown pure material/mixture and the spectra of a multitude of known pure materials/mixtures (e.g., up to 100,000 or more) stored in a database. Because the spectrum for each unknown and known pure material/mixture can have up to 2000 or more spectral intensity values, the memory requirements for storing the spectra of the unknown and known pure materials/mixtures can be high. Likewise, the processing time required to execute algorithms using such large spectral data sets based on the traditional cross correlation, Euclidean, and derivative techniques can be high, making such algorithms impractical for use in portable (e.g., hand-held) spectroscopic instruments.

SUMMARY

In accordance with the present application, apparatus and methods of spectral searching are disclosed that employ coefficients of a discrete wavelet transform (also referred to herein as "wavelet coefficients") as the basis for the searching. The disclosed apparatus and methods can transform, using a wavelet lifting scheme, spectroscopic data corresponding to an unknown pure material or mixture to a vector of wavelet coefficients, compare the wavelet coefficient vector for the unknown pure material/mixture with a library of wavelet coefficient vectors for a multitude of known pure materials/mixtures, and identify the closest match to the unknown pure material/mixture based on the comparison of wavelet coefficient vectors. Because the wavelet lifting scheme can be used to generate the wavelet coefficient vector for the unknown pure material/mixture, as well as the wavelet coefficient vectors for the known pure materials/mixtures, to conform to a desired compression level, the disclosed apparatus and methods can perform such spectral searching with increased speed and reduced memory requirements, thereby making the disclosed apparatus and methods amenable for use not only in conjunction with laboratory spectroscopic instruments, but also portable (e.g., hand-held) spectroscopic instruments for on-site material identification.

In one aspect, the disclosed method of spectral searching includes acquiring spectroscopic data for an unknown pure material or mixture. For example, the spectroscopic data for the unknown pure material/mixture may be acquired using any suitable spectroscopy technique, such as the Raman, infrared, near infrared, or fluorescence spectroscopy technique. In the event the Raman spectroscopy technique is employed, the spectroscopic data for the unknown pure material/mixture can include a sequence of intensity values that can be plotted against corresponding wavenumbers, forming a spectral plot characterized by one or more peak intensity values at corresponding wavenumbers. The disclosed method then employs the wavelet lifting scheme to provide a spatial domain interpretation of the discrete wavelet transform. The wavelet transform process described herein inherently weights most heavily the natural peak characteristics of most spectroscopic interest, such as heights, locations, and/or sharpness of the spectral peaks, and transforms the data to one or more vectors of wavelet coefficients. It is noted that certain peak characteristics, such as the locations and sharpness of the spectral peaks, can be particularly informative when performing qualitative spectral matching.

In an exemplary aspect, the wavelet lifting scheme can transform the spectroscopic data for the unknown pure material/mixture to one or more wavelet coefficient vectors by first splitting the sequence of intensity values into a first set of intensity values and a second set of intensity values. The wavelet lifting scheme can then perform a lifting wavelet "predict" process on the first set of intensity values using at least some of the second set of intensity values to generate a first set of so-called detail wavelet coefficients (also referred to herein as the "detail coefficients"), and perform a lifting wavelet "update" process on the second set of intensity values using at least some of the set of detail coefficients to generate a first set of so-called approximation wavelet coefficients (also referred to herein as the "approximation coefficients"). The first set of detail coefficients and the first set of approximation coefficients (collectively referred to herein as the "first level of wavelet coefficients") constitute a first wavelet coefficient vector for the unknown pure material/mixture.

The wavelet lifting scheme can also perform the predict process and the update process recursively to generate one or more additional levels of wavelet coefficients for the unknown pure material/mixture. For example, the wavelet lifting scheme can split the first set of approximation coefficients into a first set of coefficients and a second set of coefficients, perform the predict process on the first set of coefficients using at least some of the second set of coefficients to generate a second set of detail coefficients, and perform the update process on the second set of coefficients using at least some of the second set of detail coefficients to generate a second set of approximation coefficients. The second set of detail coefficients and the second set of approximation coefficients (collectively referred to herein as the "second level of wavelet coefficients") constitute a second wavelet coefficient vector for the unknown pure material/mixture.

It is noted that, each time the wavelet lifting scheme recursively performs the predict and update processes to generate an additional wavelet coefficient vector containing a next level of wavelet coefficients for the unknown pure material/mixture, the number of approximation coefficients from the prior level of wavelet coefficients is halved. In an exemplary aspect, the wavelet lifting scheme can recursively repeat the predict and update processes until a final wavelet coefficient vector is generated that contains a final level of wavelet coefficients, including a single approximation coefficient and one or more detail coefficients. The single approximation coefficient in the final level of wavelet coefficients corresponds to the average of the intensity values for the unknown pure material/mixture, and the one or more detail coefficients in the final level of wavelet coefficients can correspond to a single detail coefficient generated at the final level of wavelet coefficients, as well as the detail coefficients that were generated at each preceding level of wavelet coefficients for the unknown pure material/mixture. In a similar fashion, the wavelet lifting scheme can be employed to generate a final wavelet coefficient vector for each of the multitude of known pure materials/mixtures for subsequent storage in the library, which may be a database library.

In a further exemplary aspect, the disclosed method can employ the single approximation coefficient and a selected number of the levels of detail coefficients in each of the final wavelet coefficient vectors for the unknown and known pure materials/mixtures as the basis for spectral searching, thereby conforming the respective wavelet coefficient vectors for the unknown and known pure materials/mixtures to a desired compression level. The disclosed method can then compare the wavelet coefficient vector for the unknown pure material/mixture with the library of wavelet coefficient vectors for the known pure materials/mixtures, and identify the closest match to the unknown pure material/mixture based on the comparison of wavelet coefficient vectors, each conforming to the desired compression level. Such use of wavelet coefficient vectors for the unknown and known pure materials/mixtures can enable the disclosed apparatus and methods to perform spectral searching with increased speed and reduced memory requirements.

In another exemplary aspect, after the wavelet lifting scheme performs the predict and update processes on the original set of intensity values and the subsequent sets of approximation coefficients for the unknown and known pure materials/mixtures, the wavelet lifting scheme can perform a lifting wavelet "interpolation" process, such as a Lagrangian interpolation process, on the resulting set of detail coefficients using at least some of the set of approximation coefficients to obtain improved frequency separation.

In a further aspect, the disclosed apparatus can include a system bus, at least one processor coupled to the system bus, at least one memory communicably coupled to the processor and operative to store an operating system as well as data and programming instructions for performing the disclosed method of spectral searching, at least one storage medium coupled to the system bus for storage of the library of known pure materials/mixtures, a display coupled to the system bus, and an input device such as a keyboard or one or more pushbuttons and/or switches communicably coupled to the system bus. For example, the disclosed apparatus can be implemented as part of a computerized spectroscopic instrument configured for laboratory use, or as part of a portable or hand-held spectroscopic instrument for use in on-site identification of unknown materials.

BRIEF DESCRIPTION OF THE DRAWINGS

The accompanying drawings, which are incorporated in and constitute a part of this specification, illustrate one or more embodiments described herein and, together with the Detailed Description, explain these embodiments. In the drawings.

DETAILED DESCRIPTION

Apparatus and methods of spectral searching are disclosed that employ coefficients of a discrete wavelet transform (also referred to herein as "wavelet coefficients") as the basis for the searching. The disclosed apparatus and methods can transform, using a wavelet lifting scheme, spectroscopic data corresponding to an unknown pure material or mixture (also referred to herein as the "unknown sample") to a vector of wavelet coefficients, compare the wavelet coefficient vector for the unknown sample with a library of wavelet coefficient vectors for a multitude of known pure materials/mixtures (also referred to herein as the "known samples"), and identify the closest match to the unknown sample based on the comparison of wavelet coefficient vectors. Because the wavelet lifting scheme can be used to generate the wavelet coefficient vector for the unknown sample, as well as the wavelet coefficient vectors for the multitude of known samples, to conform to a desired compression level, the disclosed apparatus and methods can perform such spectral searching with increased speed and reduced memory requirements, thereby making the disclosed apparatus and methods amenable for use not only in conjunction with laboratory spectroscopic instruments, but also portable (e.g., hand-held) spectroscopic instruments for on-site material identification.

An exemplary method of performing spectral searching is described below with reference to FIGS. 1a and 1b, in accordance with the present application. As depicted in block 102, spectroscopic data for an unknown pure material or mixture is acquired using any suitable spectroscopy technique, such as the Raman, infrared, near infrared, or fluorescence spectroscopy technique. In the event the Raman spectroscopy technique is employed, the spectroscopic data for the unknown pure material/mixture can include a sequence of intensity values that can be plotted against corresponding wavenumbers, forming a spectral plot characterized by one or more peak intensity values (also referred to herein as "peaks") at corresponding wavenumbers. The exemplary method then employs a wavelet lifting scheme to provide a spatial domain interpretation of a discrete wavelet transform. The wavelet transform process described herein inherently weights most heavily the natural peak characteristics of most spectroscopic interest, such as heights, locations, and/or sharpness of the spectral peaks, and transforms the data to one or more vectors of wavelet coefficients. For example, the discrete wavelet transform can be a single 2-dimensional (2-D) discrete wavelet transform, two 1-dimensional (1-D) discrete wavelet transforms cascaded in the vertical and horizontal spatial directions, or any other suitable wavelet transform. It is noted that certain peak characteristics, such as the locations and sharpness of the spectral peaks, can be particularly informative when performing qualitative spectral matching.

As depicted in block 104, the wavelet lifting scheme transforms the spectroscopic data for the unknown pure material/mixture to one or more wavelet coefficient vectors by first splitting the sequence of intensity values into a first set of intensity values (also referred to herein as the "odd set" or "$x_{k(k\ odd)}$", in which "k" is an odd positive integer) and a second set of intensity values (also referred to herein as the "even set" or "$x_{k(k\ even)}$", in which "k" is an even non-negative integer). As depicted in block 106, the wavelet lifting scheme then performs a lifting wavelet "predict" process on the odd set of intensity values using at least some of the even set of intensity values to generate a first set of so-called detail wavelet coefficients (also referred to herein as the "detail coefficients").

For example, the predict process may be expressed in a general form, as follows:

$$d = x_{k(k\ odd)} - P(x_{k(k\ even)}), \quad (1)$$

in which "d" corresponds to the set of detail coefficients, "$x_{k(k\ odd)}$" corresponds to the odd set of intensity values, "$x_{k(k\ even)}$" corresponds to the even set of intensity values, and "P( . . . )" corresponds to the operator for the predict process. In one embodiment, the operator, P( . . . ), for the predict process can be configured to calculate the average of two neighboring elements of the even set of intensity values, $x_{k(k\ even)}$, as follows:

$$d_k = x_{2k+1} - (x_{2k} + x_{2k+2})/2, \quad (2)$$

in which "k" is a non-negative integer. In some embodiments, the operator, P( . . . ), for the predict process may be a linear operator, an operator that conforms to the Harr transform, an operator that conforms to Qspline normalization, or any other suitable operator.

As depicted in block 108, the wavelet lifting scheme further performs a lifting wavelet "update" process on the even set of intensity values, $x_{k(k\ even)}$, using at least some of the set of detail coefficients, d, to generate a first set of so-called approximation wavelet coefficients (also referred to herein as the "approximation coefficients").

For example, the update process may be expressed in a general form, as follows:

$$S = x_{k(k\ even)} + U(d), \quad (3)$$

in which "s" corresponds to the set of approximation coefficients, "$x_{k(k\ even)}$" corresponds to the even set of intensity values, and "U( . . . )" corresponds to the operator for the update process. In one embodiment, the operator, U( . . . ), for the update process can be configured as follows:

$$s_k = x_{2k} + (d_{k-1} + d_k)/4, \quad (4)$$

in which "k" is a non-negative integer. In some embodiments, the operator, U( . . . ), for the update process may be a linear operator, an operator that conforms to the Harr transform, an operator that conforms to Qspline normalization, or any other suitable operator. The first set of detail coefficients, $d_k$, and the first set of approximation coefficients, $s_k$, (collectively referred to herein as the "first level of wavelet coefficients") constitute a first wavelet coefficient vector for the unknown pure material/mixture.

Figure 1A:
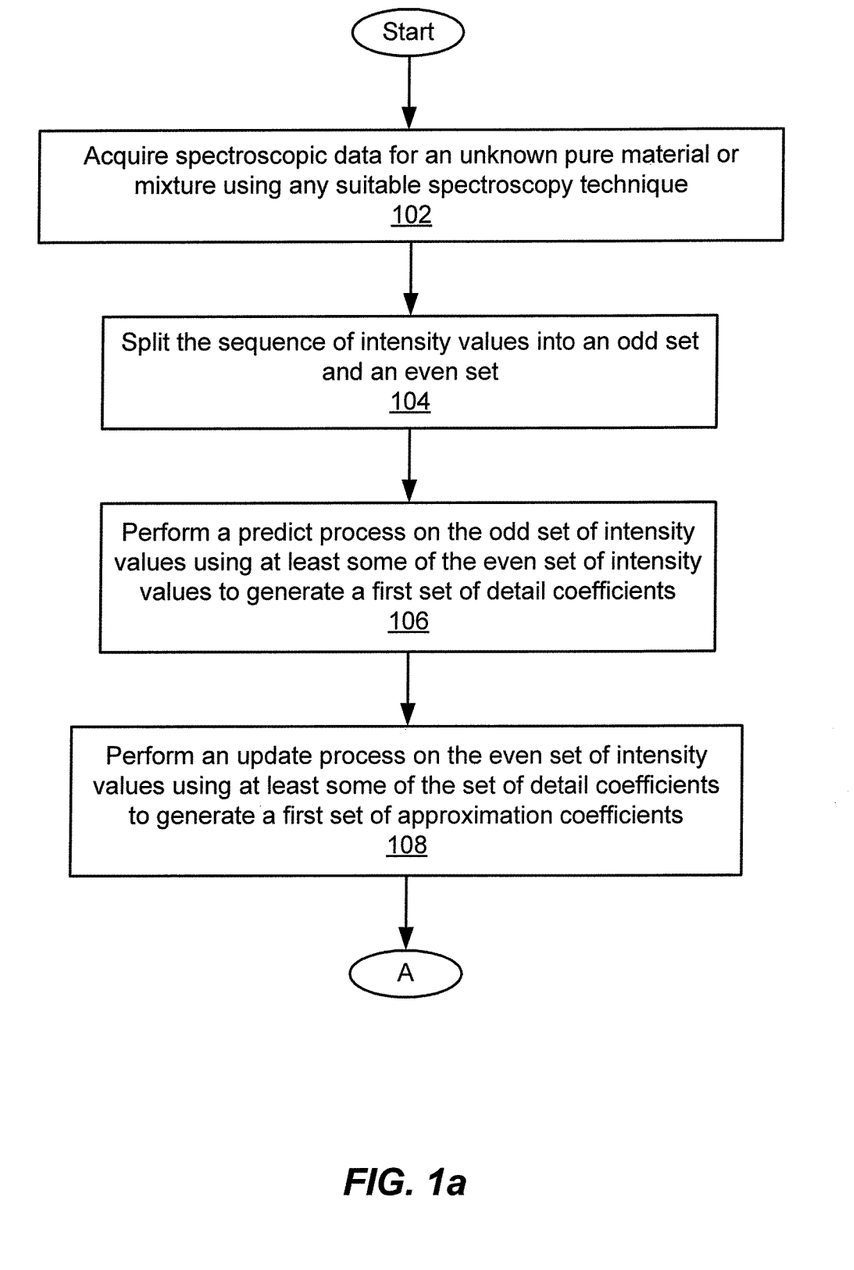
FIGS. 1a and 1b are a flow diagram illustrating an exemplary method of performing spectral searching, in accordance with the present application.
Figure 1B:
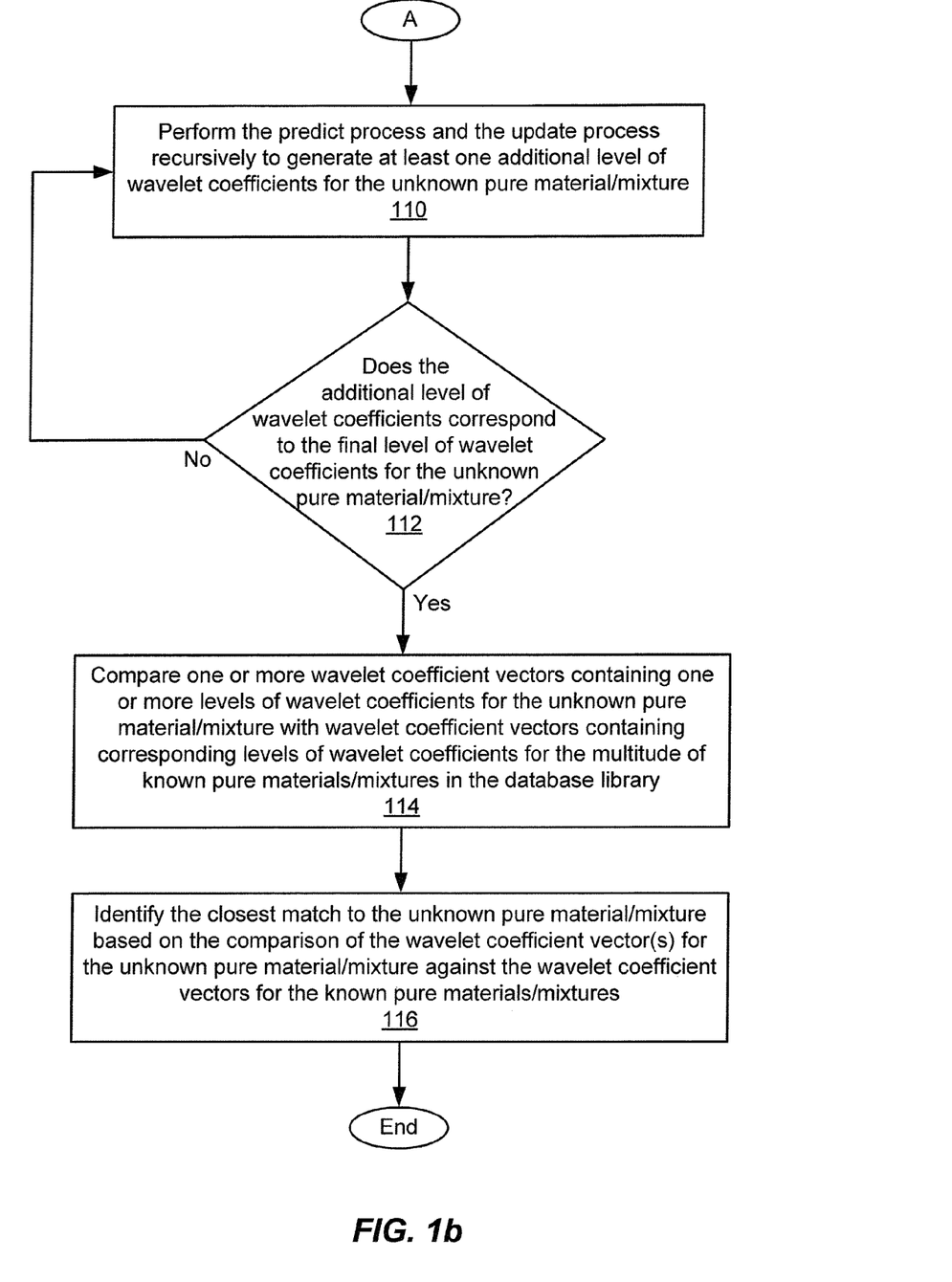
Figure 2:
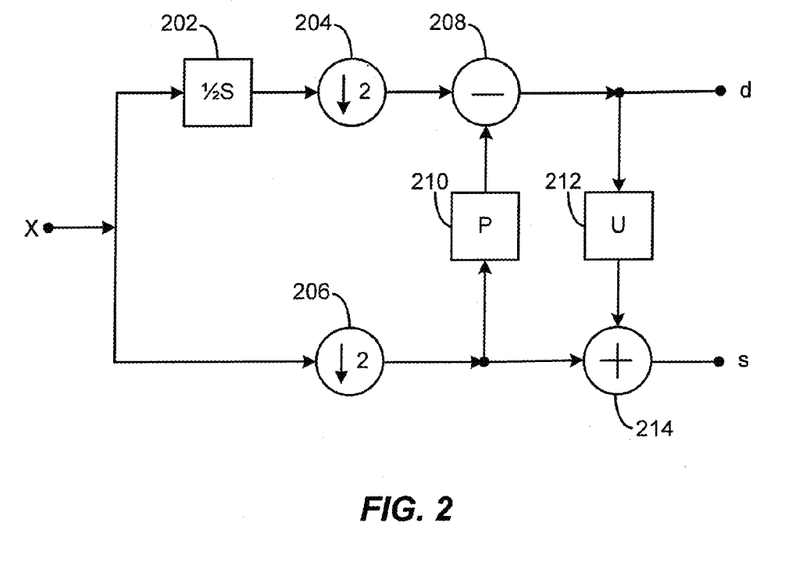
FIG. 2 diagrammatically illustrates an exemplary wavelet lifting scheme employed in the method of FIGS. 1a and 1b.

FIG. 2 diagrammatically illustrates the splitting of the sequence of intensity values, the performing of the predict process, and the performing of the update process, as depicted in blocks 104, 106, and 108, respectively, of the exemplary method of FIGS. 1a and 1b. With reference to FIG. 2, "X" corresponds to the sequence of intensity values acquired using, for example, the Raman spectroscopy technique at each corresponding wavenumber. In the diagram of FIG. 2, it is assumed that the intensity values, X, are evenly spaced in the horizontal (wavelength) spatial direction, and that the number of intensity values, X, in the sequence is evenly divisible by factors of two. In one embodiment, in the event the number of intensity values, X, in the sequence is not evenly divisible by factors of two, the sequence can be extended by copying the last intensity value in the sequence to one or more next incremental positions in the sequence while maintaining the same spread of intensity values in the horizontal (wavelength) spatial direction, until the resulting number of intensity values, X, in the sequence is evenly divisible by factors of two.

With further reference to FIG. 2, block 202 ("½S") and block 204 ("↓2") operate on the sequence of intensity values, X, to shift the sequence by one intensity value and to split the sequence in two, resulting in the odd set of intensity values, $x_{k(k\ odd)}$. Block 206 ("↓2") operates on the sequence of intensity values, X, to split the sequence in two, resulting in the even set of intensity values, $x_{k(k\ even)}$. Block 208 ("−") and block 210 ("P") operate on the even set of intensity values, $x_{k(k\ even)}$, to perform the predict process in accordance with equation (1), generating the set of detail coefficients, d. Block 212 ("U") and block 214 ("+") operate on the odd set of intensity values, $x_{k(k\ odd)}$, to perform the update process in accordance with equation (3), generating the set of approximation coefficients, s. It is noted that the sequence of operations used to generate the set of detail coefficients, d, and the set of approximation coefficients, s, can be mathematically reversed to reconstruct the original sequence of intensity values, X.

As depicted in block 110 (see FIG. 1b), the wavelet lifting scheme can perform the predict process and the update process recursively to generate at least one additional level of wavelet coefficients for the unknown pure material/mixture. For example, the wavelet lifting scheme can split the first set of approximation coefficients into a set of odd approximation coefficients and a set of even approximation coefficients, perform the predict process on the set of odd approximation coefficients using at least some of the set of even approximation coefficients to generate a second set of detail coefficients, and perform the update process on the set of even approximation coefficients using at least some of the second set of detail coefficients to generate a second set of approximation coefficients. The second set of detail coefficients and the second set of approximation coefficients (collectively referred to herein as the "second level of wavelet coefficients") constitute a second wavelet coefficient vector for the unknown pure material/mixture.

It is noted that, at each level of wavelet coefficients for the unknown pure material/mixture, the set of detail coefficients includes one or more detail coefficients generated at that level of wavelet coefficients, in addition to the detail coefficients that were generated at each preceding level of wavelet coefficients, if any. It is further noted that the values of the respective wavelet coefficients can be integer values, single-precision floating point values, double-precision floating point values, or any other suitable values. Moreover, each time the wavelet lifting scheme recursively performs the predict and update processes to generate an additional wavelet coefficient vector containing a next level of wavelet coefficients, the number of approximation coefficients from the preceding level of wavelet coefficients is halved.

In one embodiment, the wavelet lifting scheme can recursively repeat the predict and update processes until a final wavelet coefficient vector is generated that contains a final level of wavelet coefficients, including a single approximation coefficient and a plurality of detail coefficients for the unknown pure material/mixture. In the final level of wavelet coefficients, the single approximation coefficient corresponds to the average of the intensity values for the unknown pure material/mixture, and the plurality of detail coefficients can correspond to a single detail coefficient generated at the final level of wavelet coefficients, as well as the detail coefficients that were generated at each preceding level of wavelet coefficients. In a similar fashion, the wavelet lifting scheme can be employed to generate a final wavelet coefficient vector for each of the multitude of known pure materials/mixtures for subsequent storage in the library, which may be a database library.

As depicted in block 112, a determination is made as to whether or not the additional level of wavelet coefficients generated at block 110 corresponds to the final level of wavelet coefficients for the unknown pure material/mixture. In the event the additional level of wavelet coefficients for the unknown pure material/mixture does not correspond to the final level of wavelet coefficients for the unknown pure material/mixture, the exemplary method loops back to block 110 to generate the next level of wavelet coefficients for the unknown pure material/mixture. Otherwise, if the additional level of wavelet coefficients generated at block 110 corresponds to the final level of wavelet coefficients for the unknown pure material/mixture, then the generation of the wavelet coefficients for the unknown pure material/mixture is completed, and the exemplary method proceeds to block 114.

At block 114, one or more wavelet coefficient vectors containing one or more levels of wavelet coefficients for the unknown pure material/mixture are compared with wavelet coefficient vectors containing corresponding levels of wavelet coefficients for the multitude of known pure materials/mixtures in the library. Further, at block 116, the closest match to the unknown pure material/mixture is identified based on the comparison of the wavelet coefficient vector(s) for the unknown pure material/mixture against the wavelet coefficient vectors for the known pure materials/mixtures.

In one embodiment, the final wavelet coefficient vectors for the unknown and known pure materials/mixtures, each containing a single approximation coefficient and a selected number of the respective levels of detail coefficients, are employed as the basis for spectral searching, thereby conforming the wavelet coefficient vectors for the unknown and known pure materials/mixtures to a desired compression level. Such use of the final wavelet coefficient vectors for the unknown and known pure materials/mixtures can enable the exemplary method of FIGS. 1a and 1b to perform spectral searching with increased speed and reduced memory requirements.

The exemplary method of spectral searching described herein will be further understood with reference to the following illustrative example, as well as FIGS. 1a and 1b. In this example, the spectroscopic data for the unknown pure material/mixture acquired at block 102 (see FIG. 1a) can include a sequence of sixteen (16) intensity values, $x_0$ to $x_{15}$, which may be expressed, as follows:

| $x_0$ | $x_1$ | $x_2$ | $x_3$ | $x_4$ | $x_5$ | $x_6$ | $x_7$ | $x_8$ | $x_9$ | $x_{10}$ | $x_{11}$ | $x_{12}$ | $x_{13}$ | $x_{14}$ | $x_{15}$ |
|---|---|---|---|---|---|---|---|---|---|---|---|---|---|---|---|

At block 104 (see FIG. 1a), the (16) intensity values, $x_0$ to $x_{15}$, can be split into an odd set of intensity values, $x_1$, $x_3$, $x_5$, $x_7$, $x_9$, $x_{11}$, $x_{13}$, $x_{15}$, and an even set of intensity values, $x_0$, $x_2$, $x_4$, $x_6$, $x_5$, $x_{10}$, $x_{12}$, $x_{14}$, as follows:

| $x_1$ | $x_3$ | $x_5$ | $x_7$ | $x_9$ | $x_{11}$ | $x_{13}$ | $x_{15}$ | $x_0$ | $x_2$ | $x_4$ | $x_6$ | $x_8$ | $x_{10}$ | $x_{12}$ | $x_{14}$ |
|---|---|---|---|---|---|---|---|---|---|---|---|---|---|---|---|

At block 106 (see FIG. 1a), the predict process can be performed on the odd set of intensity values, $x_1$, $x_3$, $x_5$, $x_7$, $x_9$, $x_{11}$, $x_{13}$, $x_{15}$, using at least some of the even set of intensity values, $x_0$, $x_2$, $x_4$, $x_6$, $x_5$, $x_{10}$, $x_{12}$, $x_{14}$, to generate the first set of detail coefficients, $d_0$, $d_1$, $d_2$, $d_3$, $d_4$, $d_5$, $d_6$, $d_7$. Further, at block 108 (see FIG. 1a), the update process can be performed on the even set of intensity values, $x_0$, $x_2$, $x_4$, $x_6$, $x_8$, $x_{10}$, $x_{12}$, $x_{14}$, using at least some of the first set of detail coefficients, $d_0$, $d_1$, $d_2$, $d_3$, $d_4$, $d_5$, $d_6$, $d_7$, to generate the first set of approximation coefficients, $s_0$, $s_1$, $s_2$, $s_3$, $s_4$, $s_5$, $s_6$, $s_7$. The first level of wavelet coefficients for the unknown pure material/mixture can therefore be expressed, as follows:

| $s_0$ | $s_1$ | $s_2$ | $s_3$ | $s_4$ | $s_5$ | $s_6$ | $s_7$ | $d_0$ | $d_1$ | $d_2$ | $d_3$ | $d_4$ | $d_5$ | $d_6$ | $d_7$ |
|---|---|---|---|---|---|---|---|---|---|---|---|---|---|---|---|

At block 110 (see FIG. 1b), the predict process and the update process can be performed recursively to generate additional levels of wavelet coefficients for the unknown pure material/mixture. For example, the first set of approximation coefficients, $s_0$, $s_1$, $s_2$, $s_3$, $s_4$, $s_5$, $s_6$, $s_7$, from the first level of wavelet coefficients can be split into a set of odd approximation coefficients, $s_1$, $s_3$, $s_5$, $s_7$, and a set of even approximation coefficients, $s_0$, $s_2$, $s_4$, $s_6$, as follows:

| $s_1$ | $s_3$ | $s_5$ | $s_7$ | $s_0$ | $s_2$ | $s_4$ | $s_6$ | $d_0$ | $d_1$ | $d_2$ | $d_3$ | $d_4$ | $d_5$ | $d_6$ | $d_7$ |
|---|---|---|---|---|---|---|---|---|---|---|---|---|---|---|---|

Further, the predict process can be performed on the odd set of approximation coefficients, $s_1$, $s_3$, $s_5$, $s_7$, using at least some of the even set of approximation coefficients, $s_0$, $s_2$, $s_4$, $s_6$, to generate the second set of detail coefficients, $d_{20}$, $d_{21}$, $d_{22}$, $d_{23}$. The update process can also be performed on the even set of approximation coefficients, $s_0$, $s_2$, $s_4$, $s_6$, using at least some of the second set of detail coefficients, $d_{20}$, $d_{21}$, $d_{22}$, $d_{23}$, to generate the second set of approximation coefficients, $s_{20}$, $s_{21}$, $s_{22}$, $s_{23}$. The second level of wavelet coefficients for the unknown pure material/mixture can therefore be expressed, as follows:

| $s_{20}$ | $s_{21}$ | $s_{22}$ | $s_{23}$ | $d_{20}$ | $d_{21}$ | $d_{22}$ | $d_{23}$ | $d_0$ | $d_1$ | $d_2$ | $d_3$ | $d_4$ | $d_5$ | $d_6$ | $d_7$ |
|---|---|---|---|---|---|---|---|---|---|---|---|---|---|---|---|

Likewise, the second set of approximation coefficients, $s_{20}$, $s_{21}$, $s_{22}$, $s_{23}$, from the second level of wavelet coefficients can be split into a set of odd approximation coefficients, $s_{21}$, $s_{23}$, and a set of even approximation coefficients, $s_{20}$, $s_{22}$, as follows:

| $s_{21}$ | $s_{23}$ | $s_{20}$ | $s_{22}$ | $d_{20}$ | $d_{21}$ | $d_{22}$ | $d_{23}$ | $d_0$ | $d_1$ | $d_2$ | $d_3$ | $d_4$ | $d_5$ | $d_6$ | $d_7$ |
|---|---|---|---|---|---|---|---|---|---|---|---|---|---|---|---|

Further, the predict process can be performed on the odd set of approximation coefficients, $s_{21}$, $s_{23}$, using at least some of the even set of approximation coefficients, $s_{20}$, $s_{22}$, to generate a third set of detail coefficients, $d_{30}$, $d_{31}$. The update process can also be performed on the even set of approximation coefficients, $s_{20}$, $s_{22}$, using at least some of the third set of detail coefficients, $d_{30}$, $d_{31}$, to generate a third set of approximation coefficients, $s_{30}$, $s_{31}$. The third level of wavelet coefficients for the unknown pure material/mixture can therefore be expressed, as follows:

| $s_{30}$ | $s_{31}$ | $d_{30}$ | $d_{31}$ | $d_{20}$ | $d_{21}$ | $d_{22}$ | $d_{23}$ | $d_0$ | $d_1$ | $d_2$ | $d_3$ | $d_4$ | $d_5$ | $d_6$ | $d_7$ |
|---|---|---|---|---|---|---|---|---|---|---|---|---|---|---|---|

In addition, the predict process can be performed on the odd set of approximation coefficients, $s_{31}$, using the even set of approximation coefficients, $s_{30}$, to generate a fourth set of detail coefficients, $d_{40}$. The update process can also be performed on the even set of approximation coefficients, $s_{30}$, using the third set of detail coefficients, $d_{40}$, to generate a fourth set of approximation coefficients, $s_{40}$. The fourth level of wavelet coefficients for the unknown pure material/mixture can therefore be expressed, as follows:

| $s_{40}$ | $d_{40}$ | $d_{30}$ | $d_{31}$ | $d_{20}$ | $d_{21}$ | $d_{22}$ | $d_{23}$ | $d_0$ | $d_1$ | $d_2$ | $d_3$ | $d_4$ | $d_5$ | $d_6$ | $d_7$ |
|---|---|---|---|---|---|---|---|---|---|---|---|---|---|---|---|

Because the fourth level of wavelet coefficients includes the single approximation coefficient, $s_{40}$, and the single detail coefficient, $d_{40}$, generated at the fourth level of wavelet coefficients, as well as the detail coefficients, $d_{30}$, $d_{31}$, generated at the third level of wavelet coefficients, the detail coefficients, $d_{20}$, $d_{21}$, $d_{22}$, $d_{23}$, generated at the second level of wavelet coefficients, and the detail coefficients, $d_0$, $d_1$, $d_2$, $d_3$, $d_4$, $d_5$, $d_6$, $d_7$, generated at the first level of wavelet coefficients, the fourth level of wavelet coefficients corresponds to the final level of wavelet coefficients for the unknown pure material/mixture. As described herein, the single approximation coefficient, $s_{40}$, included in the final level of wavelet coefficients corresponds to the average intensity value for the unknown pure material/mixture.

The single approximation coefficient, $s_{40}$, and a selected number of the respective levels of detail coefficients, namely, $d_{40}$ ($4^{th}$ level); $d_{30}$, $d_{31}$ ($3^{rd}$ level); $d_{20}$, $d_{21}$, $d_{22}$, $d_{23}$ ($2^{nd}$ level); and, $d_0$, $d_1$, $d_2$, $d_3$, $d_4$, $d_5$, $d_6$, $d_7$ ($1^{st}$ level), may be employed as the basis for spectral searching, conforming the wavelet coefficient vectors for the unknown pure material/mixture (as well as the wavelet coefficient vectors for the known pure materials/mixtures from the library) to a desired compression level. In this example, four (4) elements from the final level of wavelet coefficients for the unknown pure material/mixture, namely, the single approximation coefficient, 540, and two levels of detail coefficients, namely, $d_{40}$ ($4^{th}$ level) and $d_{30}$, $d_{31}$ ($3^{rd}$ level), can be employed as the basis for spectral searching, thereby effectively increasing the speed and reducing the memory requirements for such spectral searching by a factor of 4 (16÷4=4). It is noted that the spectroscopic data for the unknown pure material/mixture acquired at block 102 (see FIG. 1a) includes the sequence of sixteen (16) intensity values, $x_0$ to $x_{15}$, for purposes of illustration only, and that any other suitable number of intensity values may be employed.

Having described the above exemplary embodiments of the disclosed method of spectral searching, other alternative embodiments or variations may be made. For example, to obtain improved frequency separation, the wavelet lifting scheme employed by the exemplary method described herein can perform a lifting wavelet "interpolation" process on the set of detail coefficients, d, using at least some of the set of approximation coefficients, s. For example, the interpolation process can be implemented as a Lagrangian interpolation process, such as a nominal 4-point Lagrangian interpolation process, or any other suitable interpolation process.

Figure 3:
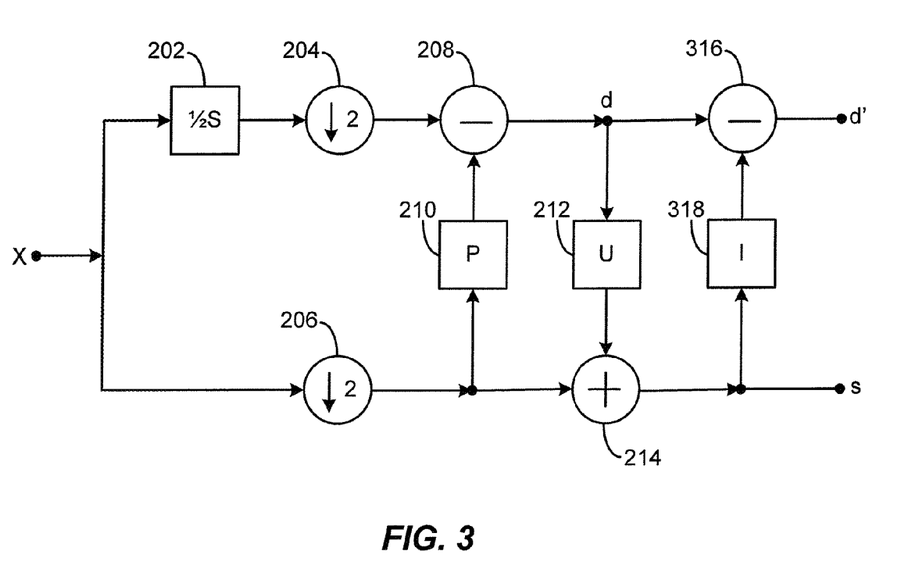
FIG. 3 diagrammatically illustrates an exemplary alternative embodiment of the wavelet lifting scheme of FIG. 2.

FIG. 3 diagrammatically that illustrates the splitting of the sequence of intensity values (or the set of approximation coefficients), the performing of the predict process, and the performing of the update process, as depicted in blocks 104, 106, and 108 (see FIG. 1a), respectively, of the above-described exemplary method of spectral searching, as well as the performing of the Lagrangian interpolation process. With reference to FIG. 3, blocks 202, 204, 206, 208, 210, 212, and 214 correspond to the same numbered blocks depicted in FIG. 2, "X" corresponds to the sequence of intensity values acquired using, for example, the Raman spectroscopy technique at each corresponding wavenumber, "d" corresponds to the set of detail coefficients, and "s" corresponds to the set of approximation coefficients.

With further reference to FIG. 3, block 316 ("−") and block 318 ("I") operate on the set of detail coefficients, d, to perform the Lagrangian interpolation process, which can be expressed in a general form, as follows:

$$d'=d-I(s), \qquad (5)$$

in which "d'" corresponds to the set of detail coefficients after being subjected to the interpolation process, and "I( . . . )" corresponds to the operator for the interpolation process. In one embodiment, the 4-point Lagrangian interpolation process can be performed by first taking the detail coefficient value, $d_k$, such that at least four (4) detail coefficient values exist before and after the value, $d_k$, and taking the four (4) approximation coefficient values, $s_{k-1}$, $s_k$, $s_{k+1}$, $s_{k+2}$, in which "k" is a non-negative integer. Next, the 4-point Lagrangian interpolation process is performed to obtain the value, $I(s_i)$ in which "i" is at the midpoint between k and k+1 (e.g., 1.5k). The value, $I(s_i)$, is then subtracted from the detail coefficient value, $d_k$, to obtain the value d', in accordance with equation (5). It is noted that such a 4-point Lagrangian interpolation process can be performed on the entire set of detail coefficients, d.

It is further noted that the 4-point Lagrangian interpolation process described herein can be performed so long as four (4) detail coefficient values, d, bound the current position, k, and at least one detail coefficient value, d, precedes the current detail coefficient value, except when the current detail coefficient value corresponds to the first detail coefficient value in the set. When the 4-point Lagrangian interpolation process is performed on the last several detail coefficients, d, in the set, such as the second to the last detail coefficient, d, in the set, the 4-point Lagrangian interpolation process can be performed to obtain the value, $I(s_i)$ in which "i" is equal to 2.5k, or any other suitable value. Further, when the 4-point Lagrangian interpolation process is performed on the last detail coefficient, d, in the set, the 4-point Lagrangian interpolation process can be performed to obtain the value, $I(s_i)$ in which "i" is equal to 3.5k, or any other suitable value.

Representative results of using the exemplary method of spectral searching described herein, as well as several traditional techniques of spectral searching, are discussed below with reference to FIGS. 4a-4c. For example, such traditional techniques of spectral searching can include spectral searching based on traditional cross correlation techniques, Euclidian techniques, derivative techniques, or any other suitable techniques.

Figure 4A:
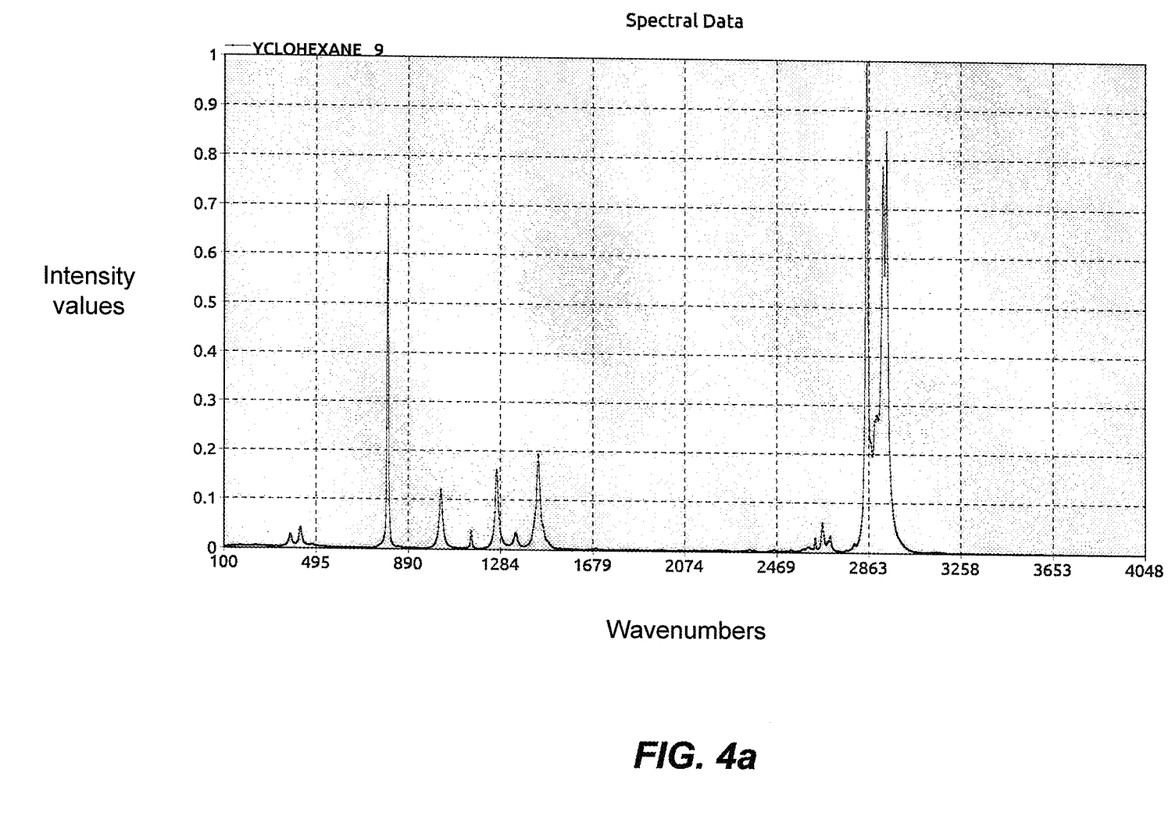
FIGS. 4a-4c are plots of spectral data for an exemplary material that can be identified using the method of FIGS. 1a and 1b.

FIG. 4a depicts a plot of spectral data for an exemplary material sample, e.g., cyclohexane, illustrating the spectral data for the cyclohexane sample with good signal-to-noise characteristics. The method of spectral searching described herein can operate on the spectral data illustrated in FIG. 4a, and identify the material sample as cyclohexane, with a hit quality index of about 1.000 (100%). Due to the good signal-to-noise characteristics of the spectral data of FIG. 4a, the traditional cross correlation, Euclidian, and derivative techniques for spectral searching may likewise be capable of identifying the material sample as cyclohexane with a hit quality index of about 1.000 (100%).

Figure 4B:
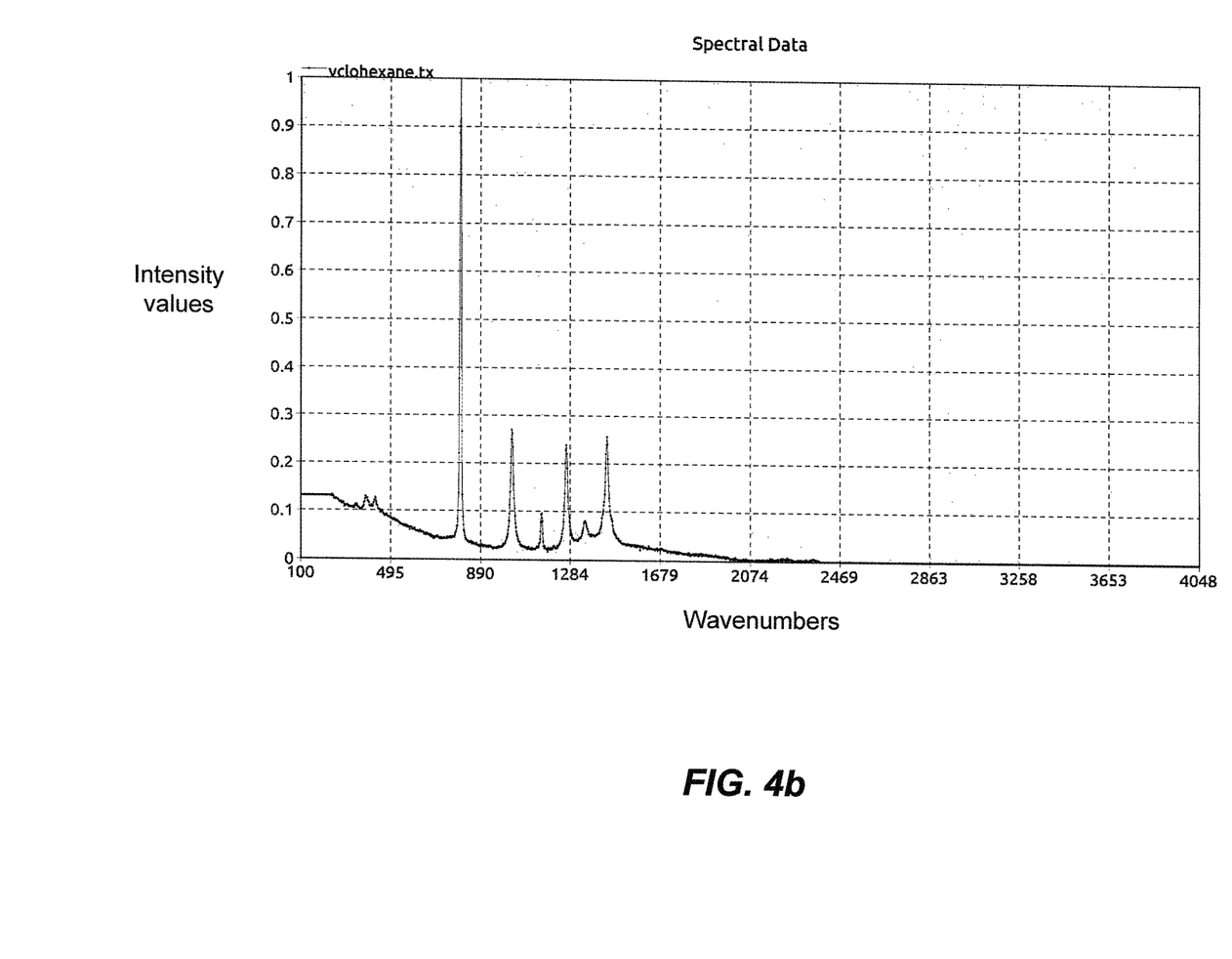

FIG. 4b depicts another plot of spectral data for the cyclohexane sample, illustrating the spectral data for the cyclohexane sample with a slight contaminant manifested as a sloping baseline between wavenumbers 100 and 2469 of the spectral plot. The method of spectral searching described herein can operate on the spectral data illustrated in FIG. 4b, and identify the material sample as cyclohexane, with a hit quality index of about 0.940 (94%). Due to the sloping baseline in the spectral data of FIG. 4b, the traditional cross correlation and derivative techniques for spectral searching may be incapable of identifying the material sample as cyclohexane, while the traditional Euclidean technique may be capable of identifying the material sample as cyclohexane with a hit quality index of about 0.680 (68%).

Figure 4C:
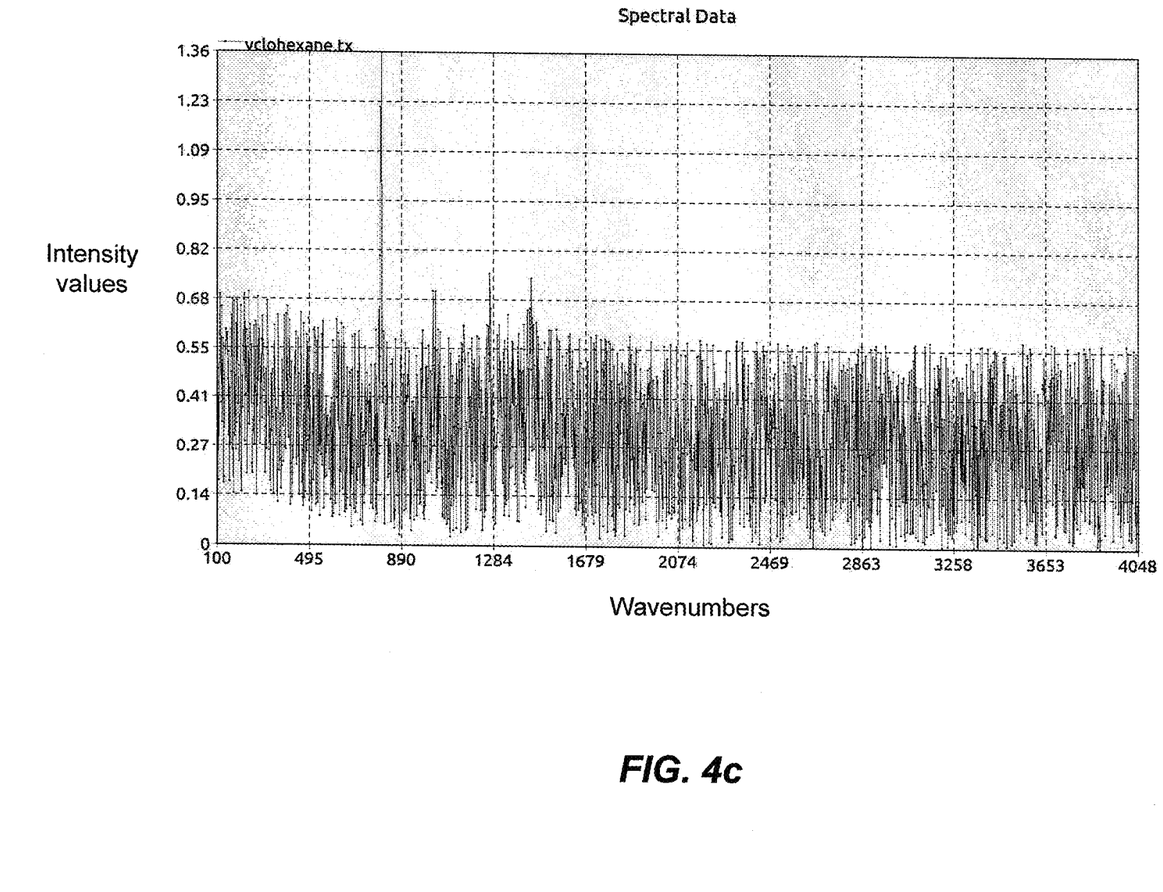

FIG. 4c depicts still another plot of spectral data for the cyclohexane sample, illustrating the spectral data for the cyclohexane sample with poor signal-to-noise characteristics. As shown in FIG. 4c, peaks in the spectral data for the cyclohexane sample are barely recognizable between wavenumbers 495 and 1679 of the spectral plot. The method of spectral searching described herein can operate on the spectral data illustrated in FIG. 4c, and identify the material sample as cyclohexane, with a hit quality index of about 0.510 (51%). Due to the poor signal-to-noise characteristics of the spectral data of FIG. 4c, the traditional cross correlation, Euclidian, and derivative techniques of spectral searching may be incapable of identifying the material sample as cyclohexane. It is noted that, in some embodiments, the exemplary method of spectral searching described herein can be employed in conjunction with traditional spectral searching methods based on cross correlation techniques, Euclidian techniques, derivative techniques, or any other suitable traditional or non-traditional techniques, for performing spectral matching.

Figure 5:
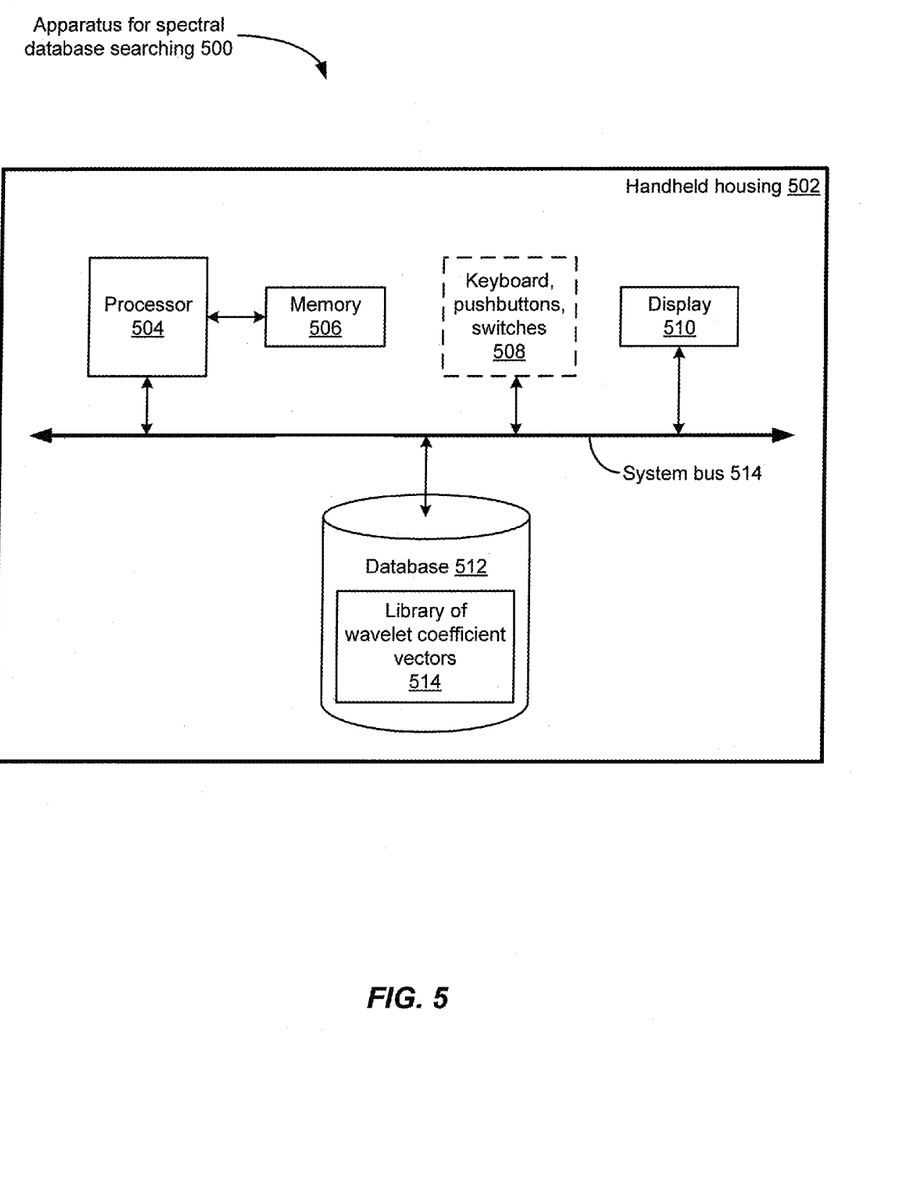
FIG. 5 is a block diagram of an exemplary apparatus configured to implement the method of FIGS. 1a and 1b.

FIG. 5 depicts an illustrative embodiment of an exemplary apparatus 500 for spectral searching, in accordance with the present application. As shown in FIG. 5, the apparatus 500 includes a system bus 514, at least one processor 504 coupled to the system bus 514, at least one memory 506 communicatively coupled to the processor 504 and operative to store an operating system as well as data and programming instructions for performing the method of spectral searching described herein, at least one database 512 coupled to the system bus 514 for storage of a library 514 of wavelet coefficient vectors for a multitude of known pure materials/mixtures, a display 510 coupled to the system bus 514, and an input device such as a keyboard or one or more pushbuttons and/or switches 508 communicably coupled to the system bus 514. For example, the various elements 504, 506, 508, 510, 512, 514 of the apparatus 500 can be implemented as part of a computerized spectroscopic instrument configured for laboratory use, or within a handheld or portable housing 502 of a spectroscopic instrument for use in on-site identification of unknown materials.

It is noted that such wavelet coefficient vectors can be stored in the database 512, in volatile or non-volatile memory using, e.g., one or more files and/or one or more binary sequences, in a cloud computing system (e.g., "in the cloud") for subsequent access through a mobile device (e.g., a laptop computer, a tablet computer, a personal digital assistant, a cell phone, a smartphone, etc.), or in any other suitable storage medium. Such a storage medium may be internal to the apparatus 500, or may be external such that it is connectable to the apparatus 500 through an interface, and/or accessible by the apparatus 500 over a wired or wireless network.

It is further noted that some portions of the preceding description may be viewed as being presented in terms of algorithms and/or symbolic representations of operations on data within a computer memory. Such algorithms are generally conceived to be sequences of operations leading to a desired result. Further, such operations are generally those requiring physical manipulations of physical quantities. Usually, though not necessarily, such quantities take the form of electrical or magnetic signals capable of being stored, transferred, combined, compared, and/or otherwise manipulated. Such signals can be referred to using terms such as bits, values, elements, symbols, characters, numbers, or the like.

Moreover, unless specifically stated otherwise, terms such as "processing", "computing", "calculating", "determining", "displaying", or the like, refer to the actions and/or processes of a computer system or similar computerized device that manipulates and transforms data, represented as physical quantities (e.g., electronic, magnetic) within the computer system's registers and/or memories, into other data similarly represented as physical quantities within the computer system's registers and/or memories, or other such information storage, transmission, and/or display devices.

The present application also relates to an apparatus for performing the operations described herein. Such an apparatus may be specially constructed for the required purpose, or it may comprise a general-purpose computer selectively activated or reconfigured by a computer program stored within the computer. Such a computer program may be stored in a machine-accessible medium, also referred to herein as a computer-readable medium, such as, but not limited to, any suitable type of disk including floppy disks, optical disks, CD-ROMs, and/or magnetic-optical disks, read-only memories (ROMs), random access memories (RAMs), EPROMs, EEPROMs, magnetic or optical cards, and/or any suitable type of media for storing electronic instructions, each coupleable to a system bus.

It is noted that the processes described herein are not inherently related to any particular computer or other apparatus. Various general-purpose systems may be used with programs in accordance with the teachings herein, or it may prove convenient to construct a more specialized apparatus to perform the operations described herein. The required structure for a variety of such systems will be evident from the above description. In addition, the present application is not described with reference to any particular programming language. It will be appreciated that a variety of programming languages may be used to implement the teachings herein.

It will be further appreciated by those of ordinary skill in the art that modifications to and variations of the above-described apparatus and methods may be made without departing from the inventive concepts disclosed herein. Accordingly, the invention should not be viewed as limited except as by the scope and spirit of the appended claims.

What is claimed is:

1. A method of spectral searching, comprising:
   transforming spectroscopic data for an unknown sample to at least one vector of wavelet coefficients;
   comparing the vector of wavelet coefficients for the unknown sample with vectors of wavelet coefficients for a multitude of known samples; and
   identifying a closest match to the unknown sample based on the comparison of the vectors of wavelet coefficients for the unknown and known samples,
   wherein the transforming of the spectroscopic data for the unknown sample includes transforming the spectroscopic data to the vector of wavelet coefficients using a wavelet lifting scheme, the spectroscopic data for the unknown sample including a sequence of spectral intensity values, and
   wherein the transforming of the spectroscopic data for the unknown sample using the wavelet lifting scheme includes:
     splitting the sequence of spectral intensity values into an odd set of spectral intensity values and an even set of spectral intensity values;
     performing a lifting wavelet predict process on the odd set of spectral intensity values using at least some of the even set of spectral intensity values to generate a first set of detail wavelet coefficients; and
     performing a lifting wavelet update process on the even set of spectral intensity values using at least some of the first set of detail wavelet coefficients to generate a first set of approximation wavelet coefficients,
   wherein the first set of detail wavelet coefficients and the first set of approximation wavelet coefficients collectively constitute a first level of wavelet coefficients, the first level of wavelet coefficients constituting a first wavelet coefficient vector for the unknown sample.

2. The method of claim 1 further comprising:
   acquiring the spectroscopic data for the unknown sample using one of a Raman spectroscopy technique, an infrared spectroscopy technique, a near infrared spectroscopy technique, and a fluorescence spectroscopy technique.

3. The method of claim 1 wherein the transforming of the spectroscopic data for the unknown sample using the wavelet lifting scheme further includes performing the lifting wavelet predict process and the lifting wavelet update process recursively to generate at least one additional level of wavelet coefficients for the unknown sample.

4. The method of claim 3 wherein the transforming of the spectroscopic data for the unknown sample using the wavelet lifting scheme further includes performing the lifting wavelet predict process and the lifting wavelet update process recursively to generate a final level of wavelet coefficients for the unknown sample, the final level of wavelet coefficients including a single approximation wavelet coefficient corresponding to an average of the spectral intensity values for the unknown sample, and a plurality of detail wavelet coefficients including a single detail wavelet coefficient for the final level of wavelet coefficients and the detail wavelet coefficients for each preceding level of wavelet coefficients.

5. The method of claim 4 wherein the transforming of the spectroscopic data for the unknown sample using the wavelet lifting scheme further includes performing the lifting wavelet predict process and the lifting wavelet update process recursively to generate the final level of wavelet coefficients for the unknown sample, the final level of wavelet coefficients including the single approximation wavelet coefficient corresponding to the average of the spectral intensity values for the unknown sample, the single detail wavelet coefficient for the final level of wavelet coefficients, and the detail wavelet coefficients for a selected number of the preceding levels of wavelet coefficients.

6. The method of claim 1 wherein the transforming of the spectroscopic data for the unknown sample using the wavelet lifting scheme further includes performing a lifting wavelet interpolation process on the first set of detail wavelet coefficients using at least some of the first set of approximation wavelet coefficients.

7. The method of claim 6 wherein the performing of the lifting wavelet interpolation process includes performing a Lagrangian interpolation process on the first set of detail wavelet coefficients using at least some of the first set of approximation wavelet coefficients.

8. An apparatus for spectral searching, comprising:
a handheld housing;
a system bus;
at least one processor coupled to the system bus;
at least one memory communicably coupled to the processor; and
a storage medium coupled to the system bus for storing a library of vectors of wavelet coefficients for a multitude of known samples,
wherein the system bus, the processor, the memory, and the storage medium are each disposed in the handheld housing, and
wherein the processor is operative to execute at least one computer program out of the memory:
to transform spectroscopic data for an unknown sample to at least one vector of wavelet coefficients;
to compare the vector of wavelet coefficients for the unknown sample with the vectors of wavelet coefficients for the multitude of known samples in the storage medium;
to identify a closest match to the unknown sample based on the comparison of the vectors of wavelet coefficients for the unknown and known samples;
to transform the spectroscopic data to the vector of wavelet coefficients using a wavelet lifting scheme, the spectroscopic data for the unknown sample including a sequence of spectral intensity values;
to split the sequence of spectral intensity values into an odd set of spectral intensity values and an even set of spectral intensity values;
to perform a lifting wavelet predict process on the odd set of spectral intensity values using at least some of the even set of spectral intensity values to generate a first set of detail wavelet coefficients; and
to perform a lifting wavelet update process on the even set of spectral intensity values using at least some of the first set of detail wavelet coefficients to generate a first set of approximation wavelet coefficients,
wherein the first set of detail wavelet coefficients and the first set of approximation wavelet coefficients collectively constitute a first level of wavelet coefficients, the first level of wavelet coefficients constituting a first wavelet coefficient vector for the unknown sample.

9. The apparatus of claim 8 wherein the processor is further operative to execute the computer program out of the memory:
to perform the lifting wavelet predict process and the lifting wavelet update process recursively to generate a final level of wavelet coefficients for the unknown sample, the final level of wavelet coefficients including a single approximation wavelet coefficient corresponding to an average of the spectral intensity values for the unknown sample, and a plurality of detail wavelet coefficients including a single detail wavelet coefficient for the final level of wavelet coefficients and the detail wavelet coefficients for each preceding level of wavelet coefficients.

10. The apparatus of claim 9 wherein the processor is further operative to execute the computer program out of the memory:
to perform the lifting wavelet predict process and the lifting wavelet update process recursively to generate the final level of wavelet coefficients for the unknown sample, the final level of wavelet coefficients including the single approximation wavelet coefficient corresponding to the average of the spectral intensity values for the unknown sample, the single detail wavelet coefficient for the final level of wavelet coefficients, and the detail wavelet coefficients for a selected number of the preceding levels of wavelet coefficients.

11. The apparatus of claim 8 wherein the storage medium includes a database for storing the library of vectors of wavelet coefficients.

12. The apparatus of claim 8 wherein the storage medium is one of a volatile memory and a non-volatile memory.

13. An apparatus for spectral searching, comprising:
a system bus;
at least one processor coupled to the system bus; and
at least one memory communicably coupled to the processor,
wherein the processor is operative to execute at least one computer program out of the memory:
to transform spectroscopic data for an unknown sample to at least one vector of wavelet coefficients;
to compare the vector of wavelet coefficients for the unknown sample with a library of vectors of wavelet coefficients for a multitude of known samples;
to identify a closest match to the unknown sample based on the comparison of the vectors of wavelet coefficients for the unknown and known samples;
to transform the spectroscopic data to the vector of wavelet coefficients using a wavelet lifting scheme, the spectroscopic data for the unknown sample including a sequence of spectral intensity values;
to split the sequence of spectral intensity values into an odd set of spectral intensity values and an even set of spectral intensity values;
to perform a lifting wavelet predict process on the odd set of spectral intensity values using at least some of the even set of spectral intensity values to generate a first set of detail wavelet coefficients; and
to perform a lifting wavelet update process on the even set of spectral intensity values using at least some of the first set of detail wavelet coefficients to generate a first set of approximation wavelet coefficients,
wherein the first set of detail wavelet coefficients and the first set of approximation wavelet coefficients collectively constitute a first level of wavelet coefficients, the first level of wavelet coefficients constituting a first wavelet coefficient vector for the unknown sample.

14. The apparatus of claim 13 further comprising:
an interface connectable to a network, and
wherein the processor is further operative to execute the computer program out of the memory to access the library of vectors of wavelet coefficients from an external storage medium over the network through the interface.

15. The apparatus of claim 14 further comprising:
a portable housing, and
wherein the system bus, the processor, and the memory are each disposed in the portable housing.

16. The apparatus of claim 15 wherein the system bus, the processor, and the memory disposed in the portable housing constitute one of a laptop computer, a tablet computer, a personal digital assistant, a cell phone, and a smartphone.

17. The apparatus of claim 13 wherein the processor is further operative to execute the computer program out of the memory:
to transform spectroscopic data acquired using a Raman spectroscopy technique to at least one vector of wavelet coefficients for the unknown sample.

* * * * *